US008802707B2

(12) United States Patent
Marshall

(10) Patent No.: US 8,802,707 B2
(45) Date of Patent: Aug. 12, 2014

(54) METHOD OF TREATING AND/OR PREVENTING CANCERS USING SARTANS AND/OR STATINS TO MODULATE VDR, AND/OR PPAR, AND/OR GCR AND/OR CB1 RECEPTORS; IN CONJUNCTION WITH CERTAIN BACTERIOSTATIC ANTIBIOTICS

(76) Inventor: Trevor Gordon Marshall, Thousand Oaks, CA (US)

(*) Notice: Subject to any disclaimer, the term of this patent is extended or adjusted under 35 U.S.C. 154(b) by 1328 days.

(21) Appl. No.: 11/309,355

(22) Filed: Jul. 31, 2006

(65) Prior Publication Data

US 2007/0149452 A1 Jun. 28, 2007

Related U.S. Application Data

(60) Provisional application No. 60/595,727, filed on Jul. 31, 2005, provisional application No. 60/597,071, filed on Nov. 8, 2005, provisional application No. 60/597,574, filed on Dec. 11, 2005.

(51) Int. Cl.
*A61K 31/4164* (2006.01)
*A61K 38/55* (2006.01)
*A61K 31/7034* (2006.01)
*A61K 31/7048* (2006.01)
*A61K 31/65* (2006.01)
*A61K 31/4184* (2006.01)

(52) U.S. Cl.
CPC ......... *A61K 31/4184* (2013.01); *A61K 31/7034* (2013.01); *A61K 31/65* (2013.01)
USPC ................ 514/382; 514/9.7; 514/35; 514/37; 514/39; 514/152; 514/394

(58) Field of Classification Search
CPC ... A61K 38/55; A61K 31/7034; A61K 31/65; A61K 31/4184; A61K 31/7048; A61K 31/7036; A61K 31/4178
USPC ................... 514/152, 12, 35, 37, 39, 394, 9.7
See application file for complete search history.

(56) References Cited

U.S. PATENT DOCUMENTS

| | | | | |
|---|---|---|---|---|
| 5,563,130 | A * | 10/1996 | Backer et al. ................ | 514/152 |
| 2003/0083339 | A1* | 5/2003 | Tamura ...................... | 514/263.4 |
| 2003/0181406 | A1 | 9/2003 | Schetter et al. | |
| 2003/0199424 | A1 | 10/2003 | Smith et al. | |
| 2003/0207819 | A1 | 11/2003 | Moskowitz | |
| 2004/0097565 | A1 | 5/2004 | Terashita et al. | |
| 2004/0219208 | A1 | 11/2004 | Kawamura et al. | |
| 2005/0112638 | A1 | 5/2005 | Sandberg | |
| 2005/0119323 | A1* | 6/2005 | Kubota et al. ................ | 514/381 |
| 2006/0025358 | A1 | 2/2006 | Marshall | |
| 2006/0135422 | A1 | 6/2006 | Moskowitz | |
| 2007/0135504 | A1 | 6/2007 | Marshall | |

OTHER PUBLICATIONS

Teicher et al. (E J of Cancer, vol. 32A, 14, p. 2461-2466, 1996).*
Sotomayor et al. (Cancer Chemother Pharmacol, 1992, 30, 377-384).*
Rao (Intensive Care Med, 1998).*
Goldgerg et al. (Colorectal Cancer, A clinical guide to therapy, Ed. Harry Bleiberg, 2002, 61, p. 629, 632-633).*
(http://en.wikipedia.org/wiki/Pathogenic_bacteria), 2010.*
Garbach (infection, 10, 1982, p. 379-384).*
(http://en.wikipedia.org/wiki/Cancer_bacteria), 2010.*
Moore (App and Environmental Microbiology, 1995, 3202-3207).*
Quigley (Expert Opinion, Ther Targets, 2007, 11(4).*
Albert, P. J. et al. (2009). "Vitamin D: The Alternative Hypothesis," *Autoimmunity Reviews*, Article in Press, 6 pages.
Blaney, G. P. et al. (Submitted Jan. 9, 2009). "Vitamin D Metabolites as Clinical Markers in Autoimmune and Chronic Disease," *Annals of the New York Academy of Sciences*, unedited manuscript, 14 pages.
Marshal, T. G. et al. (2004). "Antibacterial Therapy Induces Remission in Sarcoidosis," English translation of *MKDTS* paper, pp. 1-9.
Marshall, T. G. et al. (2004). "Sarcoidosis Succumbs to Antibiotics—Implications for Autoimmune Disease," *Autoimmunity Reviews*, 3:295-300.
Marshall, T. (Apr. 18, 2009). Written transcript of "The Marshall Protocol in a Clinical Environment: Observations from the Initial Cohort" presented at Workshop on Chlamydial Infection, Prague, Czech Republic, 12 pages.
Marshall, T. (Dec. 5-7, 2008). Written transcript of "Understanding Human Disease Requires Study of a Metagenome, Not Just the Human Genome" Keynote Speech at 2008 World Gene Congress, Foshan, China, located at <http://autoimmunityresearch.org/transcripts/WCG2008_Keynote_Transcript.pdf>. (12 pages).
Marshall, T. G. et al. (Apr. 2004). "Putative Antibacterial Mechanisms for Angiotensin II Receptor Blockers," *Journal of Independent Medical Research*, located at <http://www.joimr.org/marshall-vol2-no2.pdf>, 2(2):10 pages.
Marshall, T. G. et al. (Aug. 2, 2003). "Antibiotics in Sarcoidosis—Reflections on the First Year," *Journal of Independent Medical Research*, located at <http://www.joimr.org/marshall-vol1-no3-B.pdf>, 1(5):1-8.

(Continued)

*Primary Examiner* — Kendra D Carter
*Assistant Examiner* — Jason A Deck
(74) *Attorney, Agent, or Firm* — Morrison & Foerster LLP

(57) ABSTRACT

This invention is a method of killing the stealthy intra-cellular bacteria which are key to the pathogenesis Cancers. These very tiny L-form Cell-Wall-Deficient (CWD) antibiotic-resistant bacteria live within the cytoplasm of cells, including the phagocytic cells (e.g. monocytes, macrophages, lymphocytes, neutrophils and polymorphonuclear cells) of the immune system itself. The cellular proliferation in Cancer is catalysed the action of the same tiny L-form bacteria. They cause the cell nucleus to release mRNA signaling the Th1 cytokine cascade without the need for conventional signaling via, for example, CD4+T -Lymphocytes. Some of these Cytokines and Chemokines, including, without limitation, Cellular Adhesion Molecule (CAM), create the environment which allows the cellular proliferation to start, and then allows the cancerous growth to gain a foothold in the body. Killing these stealthy pathogens removes the environment needed to initiate and feed the cellular proliferation commonly called 'Cancer'. This invention achieves its objective partly by reducing the ability of these tiny L-form, intra-phagocytic bacteria to translate proteins within their 70S Ribosome. The 30S and 50S subunits of the bacterial ribosome are targeted both individually and collectively. Further, this invention activates the innate immune system with agonist(s) for the VDR Nuclear Receptor, and modulates the availability of endogenous ligands to the PPAR, GCR and CB1 receptors, conditioning the immune system to more easily recognize and kill these tiny bacterial pathogens.

19 Claims, 13 Drawing Sheets

(56) References Cited

OTHER PUBLICATIONS

Marshall, T. G. et al. (Aug. 22, 2002). "Remission in Sarcoidosis," *Clinical Medicine & Health Research*, located at <http://clinmed.netprints.org/cgi/content/full/2002080004>. (7 pages).

Marshall, T. G. et al. (Aug. 29, 2002). "Valsartan Dosing Regime Modulates Psychotic Events in Two Sarcoidosis Patients," *Clinical Medicine & Health Research*, located at <http://clinmed.netprints.org/cgi/content/full/2002080006>. (4 pages).

Marshall, T. G. et al. (Jan. 10, 2006). "Common Angiotensin Receptor Blockers May Directly Modulate the Immune System via VDR, PPAR and CCR2b," *Theoretical Biology and Medical Modelling*, 3(1):33 pages.

Marshall, T. G. et al. (Jan. 27, 2003). "New Treatments Emerge as Sarcoidosis Yields Up its Secrets," *Clinical Medicine & Health Research*, located at <http://clinmed.netprints.org/cgi/content/full/2003010001>. (10 pages).

Mercola, J. (Sep. 14, 2002). Study Summary for "Remission in Sarcoidosis" by Marshall, T. G. et al., located at <http://articles.mercola.com/sites/articles/archive/2002/09/14/sarcoidosis.aspx>. (2 pages).

Perez, T. (Sep. 10-14, 2008). Written transcript of "MP Study Results" presented at 6th International Congress on Autoimmunity, Porto, Portugal, located at <http://autoimmunityresearch.org/transcripts/ICA2008_Transcript_TomPerez.pdf>. (4 pages).

Proal, A. D. et al. (2009). "Autoimmune Disease in the Era of the Metagenome," *Autoimmunity Reviews*, Article in Press, 5 pages.

Proal, A. D. et al. (Submitted 2009). "Dysregulation of the Vitamin D Nuclear Receptor May Contribute to the Higher Prevalence of Some Autoimmune Diseases in Women," *Annals of the New York Academy of Sciences*, unedited manuscript, 16 pages.

Restriction Requirement mailed Feb. 6, 2009, for U.S. Appl. No. 11/161,318, filed Jul. 29, 2005, 5 pages.

Autoimmunity Research Foundation (Last modified on Jul. 29, 2009). "Timeline of the Marshall Protocol," located at <http://mpkb.mp-dev.com/doku.php/home:arf:timeline> visited on Aug. 20, 2009.

Berkow et al. ed. (1992). *The Merck Manual of Diagnosis and Therapy*. Sixteenth edition, Merck Research Laboratories, p. 1083.

China Medicinal Biotech Forum 2009. "The VDR and Metastasizing Cancers," presented by Prof. Trevor Marshall. Autoimmunity Research Foundation, 8 pages.

WCG 2008 Presentation. "Understanding Human Disease requires study of a Metagenome, not just the Human Genome," presented by Prof. Trevor Marshall. Autoimmunity Research Foundation, 12 pages.

Wu et al. (Aug. 2009). "A human colonic commensal promotes colon tumorigenesis via activation of T helper type 17 T cell response," *Nature Medicine* (Advance Online Publication), pp. 1-8.

Shoman, M (Apr. 2001). "Could Antibiotics Cure Your Hashimoto's Disease?" located at <http://www.thyroid.about..com/cs/hashimotos/a/antibiotics.htm> (pp. 1-2).

"Understanding Lupus", Lupus Foundation of America, Inc., Retrieved on Jun. 4, 2010, Webpage available at: http://www.lupus.org/webmodules/webarticlesnet/templates/new_learnunderstanding.aspx?articleid=2231&zoneid=523.

Final Office Action received for U.S. Appl. No. 11/608,838, mailed on Jun. 10, 2010, 24 pages.

Non Final Office Action received for U.S. Appl. No. 11/161,318, mailed on Jul. 15, 2011, 14 pages.

Final Office Action received for U.S. Appl. No. 11/161,318, mailed on Jan. 18, 2012, 11 pages.

Final Office Action received for U.S. Appl. No. 11/161,318, mailed on May 26, 2010, 14 pages.

Clair et al., "The Effects of Intravenous Doxycycline Therapy for Rheumatoid Arthritis", Arthritis & Rheumatism, vol. 44, No. 5, May 2001, pp. 1043-1047.

Eichenfield, Andrew H., "Minocycline and Autoimmunity", Current Opinion in Pediatrics, vol. 11, 1999, pp. 447-456.

"Alzheimer's-associated protein may be part of the innate immune system", Massachusetts General Hospital, Mar. 3, 2010, Webpage available at: http://www.sciencedaily.com/releases/2010/03/100302201656.htm.

Nicolson et al., "Role of Chronic Bacterial and Viral Infections in Neurodegenerative, Neurobehavioral, Psychiatric, Autoimmune and Fatiguing Illnesses: Part 1", British Journal of Medical Practitioners, vol. 2, No. 4, Dec. 2009, pp. 20-28.

Nicolson et al., "Role of Chronic Bacterial and Viral Infections in Neurodegenerative, Neurobehavioural, Psychiatric, Autoimmune and Fatiguing Illnesses: Part 2", British Journal of Medical Practitioners, vol. 3, No. 1, Mar. 2010, pp. 301-310.

Soscia et al., "The Alzheimer's Disease-Associated Amyloid β-Protein Is an Antimicrobial Peptide", PLoS One, vol. 5, No. 3, pp. 1-10. Published 2010.

* cited by examiner

Key

● ─ ○ Ligand bond
● ─ ○ Non-ligand bond
● - 3.0 - ● Hydrogen bond & length

His 53  Non-ligand residues involved in hydrophobic contact

Atoms involved in hydrophobic contact

Key

● ─── ◉ Ligand bond
● ─── ◉ Non-ligand bond
●--3.0--● Hydrogen bond & length

His 53 ⁄⁄⁄⁄⁄ Non-ligand residues involved in hydrophobic contact
◉ Atoms involved in hydrophobic contact

METHOD OF TREATING AND/OR PREVENTING CANCERS USING SARTANS AND/OR STATINS TO MODULATE VDR, AND/OR PPAR, AND/OR GCR AND/OR CB1 RECEPTORS; IN CONJUNCTION WITH CERTAIN BACTERIOSTATIC ANTIBIOTICS

This application claims benefit of priority to the following U.S. Provisional Patent Applications, Ser. No. 60/595,727, filed Jul. 31, 2005; Ser. No. 60/597,071, filed Nov. 8, 2005; and Ser. No. 60/597,574 filed Dec. 11, 2005; each of which is incorporated herein by reference in its entirety for any purpose.

FIELD OF THE INVENTION

The present invention relates to a method for treatment and/or prevention of the diseases collectively knows as "Cancers," and/or the diseases resulting from Human Immunodeficiency Virus (HIV) infection, commonly known as "Acquired Immune Deficiency Syndrome(s)" (AIDS). This invention differs materially from prior-art in several respects, most notably as it discloses that these diseases are the result of activity of tiny, intra-phagocytic prokaryotic pathogens, and discloses methods for killing these pathogens, the root cause of the morbidity of Cancers and AIDS, thereby inducing patient recovery, and/or preventing the occurrence and/or re-occurrence of these diseases.

DEFINITION OF TERMS

The term "treat", "treating", or "treatment," in all grammatical forms, as used herein refers to the prevention, reduction, or amelioration, partial or complete alleviation, or cure of a disease, disorder, or condition, wherein prevention indicates treatment of a person at risk for developing such a disease, disorder or condition.

VDR is the commonly accepted acronym for the "Vitamin D Receptor," a type-1 nuclear receptor, active in the nucleus of many types of cells, especially phagocytes. PPAR is the "Peroxisome Proliferator Activated Receptor," another type-1 nuclear receptor, and is commonly found in subtypes alpha and gamma. GCR is the "Glucocorticoid Receptor," again a type-1 nuclear receptor.

The CB1 receptor is a G-Protein Coupled Receptor (GPCR) commonly known as a "Cannabinoid Receptor," expressed on the surface of Lymphocytes, and active in the immune system. AG2R is also a GPCR, the Angiotensin II Type 1 receptor, active in the Renin-Angiotensin System (RAS).

For the purpose of this patent and Claims, all Prokaryotic organisms shall hereinafter be termed 'bacteria,' but such term shall include all archaeal and protozoal pathogens whose genomes carry the code to create proteins functionally similar to G-Coupled Protein Receptors and Nuclear Receptors. For example, but without limitation, the archeal species 'Archaeoglobus fulgidus' contains GPCR proteins, including Swiss-Prot:O28474.

For the purpose of this specification and claims, the term "Cancers" includes AIDS Related Cancer, Anal Cancer, Bladder Cancer, Brain Tumor, Breast Cancer, Carcinoid Tumor, Cervical Cancer, Colorectal Cancer, Endometrial Cancer, Esophageal Cancer, Gallbladder Cancer, Bileduct Cancer, Gastric Cancer, Head and Neck Cancers, Hodgkin's Lymphoma, Non-Hodgkin's Lymphoma, Kidney Cancer, Laryngeal Cancer, Hypopharyngeal Cancer, Leukemia, Liver Cancer, Lung Cancer, Lymphoma, Melanoma, Mesothelioma, Metastatic Cancer, Multiple Myeloma, Nasopharyngeal Cancer, Oral Cavity Cancer, Pharynx Cancer, Ovarian Cancer, Pancreatic Cancer, Prostate Cancer, Sarcoma, Skin Cancer, Small Intestine Cancer, Testicular Cancer, Thyroid Cancer, and Thymoma, both malignant and benign.

The term "AIDS" first appeared in the *Morbidity and Mortality WeeklyReport* (*MMWR*) of the Centers for Disease Control (CDC) in 1982 to describe ". . . a disease, at least moderately predictive of a defect in cell-mediated immunity, occurring with no known cause for diminished resistance to that disease" (CDC, 1982b). The initial CDC list of AIDS-defining conditions, which included Kaposi's sarcoma (KS), Pneumocystis carinii pneumonia (PCP), *Mycobacterium avium* complex (MAC) and other conditions, has been updated on several occasions, with significant revisions (CDC, 1985a, 1987a, 1992a, et. seq.)

BACKGROUND OF THE INVENTION

It is currently believed that the disease(s) known as AIDS are caused by a virus, the Human Immunodeficiency Virus (HIV). But I have discovered that much of the destruction of the immune system in AIDS is actually caused by tiny, stealthy, antibiotic-resistant bacteria. The HIV virus weakens the immune system so that the stealthy bacteria can proliferate out-of-control, and the damage in AIDS is done just as much by these bacteria as by any virus. These very tiny L-form Cell-Wall-Deficient (CWD) antibiotic-resistant bacteria live within the cytoplasm of cells, including the phagocytic cells (e.g. monocytes, macrophages, lymphocytes, neutrophils and polymorphonuclear cells) of the immune system itself. Killing these stealthy bacteria stops the progression, can prevent re-occurrence, and can even prevent the initial occurrence, of the disease commonly known as AIDS.

It is currently believed that the diseases commonly known as Cancer, both malignant and benign, are caused by an unknown process of cellular proliferation. But I have discovered that the cellular proliferation in Cancer actually begins due to the action of the same tiny, stealthy, antibiotic-resistant bacteria as cause immune-system destruction in AIDS. These very tiny L-form Cell-Wall-Deficient (CWD) antibiotic-resistant bacteria live within the cytoplasm of cells, including the phagocytic cells (monocytes, macrophages, lymphocytes, neutrophils and polymorphonuclear cells) of the immune system itself. These bacteria cause the cell nucleus to release the mRNA signaling the Th1 cytokine cascade, without the need for conventional signaling via, for example, CD4+T-Lymphocytes. Some of these Cytokines and Chemokines, including, without limitation, Cellular Adhesion Molecule (CAM), create the environment which allows the cellular proliferation to start, and the cancerous growth to gain a foothold in the body. Killing these stealthy pathogens removes the environment needed to initiate and feed the cellular proliferation commonly called 'Cancer'.

Activation and Re-activation of the Immune System

The tiny intra-phagocytic L-form bacteria which cause these diseases were first described at Lister Institute in 1934. However, they were never identified as being pathogenic, or to cause disease. For example, an excellent description is given in: KLIENEBERGER-NOBEL E. Filterable forms of bacteria. Bacteriol Rev. 1951 Jun; 15(2):77-103. Available at URL http://www.pubmedcentral.nih.gov/articlerender.fcgi?artid=440979 but in the ensuing half-century these pathogens were not identified as the cause of disease.

This inventor is the first person to have described (in detail) the mechanisms by which such organisms are indeed pathogenic, and has devised both molecular biology and clinical trials which demonstrate that they are at the heart of much chronic disease (see the the inventor's published scientific papers in "*Special Considerations for Asserted Therapeutic or Pharmacological Utilities*" below).

The immune system is activated by a number of mechanisms in the body. One of the most important is activation of the Type-1 Nuclear Receptors in the nucleus of phagocytic cells. This activation commences the process of transcription of DNA genes into the proteins and peptides which drive both the adaptive and the innate immune responses.

The 'Vitamin D Receptor' (VDR) has many biological functions in the body, acting on hormone systems as disparate, and ubiquitous as the Para-Thyroid Hormone (PTH) and the Gonadotrophic Releasing Hormone (GnRH). It is principally activated by the seco-steroid hormone called 1,25-dihydroxyvitamin-D (1,25-D).

The VDR has a primary role to play in activation of innate immunity, as it is responsible, inter alia, for transcription of Toll-Like Receptors TLR2 and TLR4, essential for recognition of the lipoproteins and lipopolysaccharides by which the immune system senses bacteria. It is also responsible for generation of CAMP (Cathelicidin Anti-Microbial Peptide).

A biochemical or chemical compound (a 'ligand') can bind to the ligand binding domain (LBD) of the VDR and activate the receptor, or it might deactivate the receptor by binding into a position which restricts activation by its natural hormone; 1,25-D. Both activation and deactivation (agonism and antagonism) are described in this inventor's paper: Marshall T G, Lee R E, Marshall F E: *Common angiotensin receptor blockers may directly modulate the immune system via VDR, PPAR and CCR2b. Theor Biol Med Model.* 2006 Jan. 10;3(1): 1. Available from URL http.//www.tbiomed.com/content/3/1/1

In particular, an exogenous chemical agent, such as a drug from the Sartan or Statin families, can activate or deactivate VDR in this manner (as a ligand). Such a ligand can also bind into the Peroxisome Proliferator-Activated Receptor (PPAR) and the GCR. Such activation and de-activation conditions the operation of the immune system, and is effective in therapy and/or prevention of Cancers and AIDS. Table 1 shows the molecular affinities exhibited by the common Sartans and Statins for several Nuclear Receptors active in the immune system.

Note that Table 1 shows considerable difference in affinity between the various Sartans and Statins licensed by the FDA as safe for therapeutic use in their primary indications. No direct equivalence can be drawn between the members in each family of drugs. Further, it is not obvious from Table 1 whether a drug is agonistic or antagonistic to receptor activation, considerable theoretical and geometric analysis is required to deduce this. This inventor has reported that Simvastatin and Olmsartan Medoxomil are both partial agonists of the VDR—see, for example: Marshall T G . "Are Statins Analogues of Vitamin D?" Letter to the Editor, *The Lancet*, in press.

However, even though Simvastatin is a partial VDR agonist it is not as suitable as Olmesartan Medoxomil in treatment and/or prevention of Cancers and AIDS, as it does not affect other immune-system receptors in the same beneficial manner as Olmesartan Medoxomil. But it is better than nothing, as it does partly activate innate immunity.

Weakening the Pathogens.

Such chemical compounds (ligands) can independently, and/or in addition, bind into the ligand binding domain of the G-Protein Coupled Receptors (GPCRs) located in the genomes of pathogens, including bacterial, archaeal and protozoal pathogens, including the pathogens which cause morbidity in MRSA and Tuberculosis; as well as in Autoimmune Disease, Th1 immune dysfunction, Cancers and HIV/AIDS. When such prokaryotic GPCRs are blocked by ligands, the pathogenic organism cannot function correctly, and the pathogen eventually dies. Thus the blockade of the pathogen's GPCRs and NRs gives such a ligand antimicrobial and/or anti-bacterial and/or antibiotic properties. Common Sartans, and some 'Statins,' already approved by the FDA for moderate hypertension and hyperlipidemia, are just a few of the compounds which can bind into the pathogens' GPCRs and NRs. By careful selection of the Statin, Sartan, or ligand, to be used in prevention and treatment of Cancers and/or AIDS, compound can be selected which additionally have action directly against the pathogenic genomes.

Examples of such direct action of these drugs on Pathogenic genomes are shown in FIG. 1 (Olmesartan Medoxomil in MRSA SAR0276), FIG. 2 (Olmesartan Medoxomil in bb0006 from *Borrelia burgdorferl*), FIG. 3 (Olmesartan Medoxomil in rp630 from species *Rickettsia*), FIG. 4 (Olmesartan Medoxomil in *E.coli* ydgG), FIG. 5, Olmesartan Medoxomil in *Mycobacterium tuberculosis* mt1133), and FIG. 7 (Simvastatin in MRSA SAR0276).

This invention additionally provides means to kill the stealthy L-form bacteria by reducing their ability to transcribe DNA genes into proteins with their 70S Ribosome. The 30S and 50S subunits of the bacterial ribosome are targeted both individually and collectively by the antibacterial agents optionally used as part of this invention. Further, this invention reduces the availability of Angiotensin II to the Angiotensin receptors on the phagocytic outer membrane, which decreases the amount of Nuclear-Factor-kappa-B produced to fuel the transcription of Cytokines and Chemokines by the activated phagocyte.

Optimally Effective Antibiotics and Dosing Regimes

These stealthy intra-cellular bacteria are so very small they have shed parts of their physical structure (their Cell Walls), and possibly also some of their plasmids, in the transformation into the L-form pathogens. Therefore, analysis of the actions of antibiotics on these organisms can only be performed after analysis of the bacterial genome, just as was performed to obtain the analysis shown in FIGS. 1, 2, 3, 4, 5, and 7.

These L-form bacteria are very, very, difficult to culture, and conventional antibiotic sensitivity testing offers little or no help in understanding the effectiveness of this invention.

Standard antibiotic regimes do not kill these intra-phagocytic bacteria. They may therefore be thought of as "antibiotic-resistant" bacteria. As L-form bacteria they are not susceptible to antibiotics in most common use, the 'bactericidal' antibiotics. See, for example:

Dienes L, et al: The Transformation of Typhoid Bacilli into L Forms under Various Conditions. J Bacteriol. 1950 June; 59(6): 755-764. PMID: 15436450

Dienes L: The Isolation of L Type Cultures from Bacteroides with the Aid of Penicillin and Their Reversion into the Usual Bacilli. J Bacteriol. 1948 Oct; 56(4): 445-456. PMID:1 6561 593

This invention can kill these antibiotic-resistant bacteria. One problem is that as the bacteria are killed they release endotoxins, and/or other toxic biochemicals, into the cytoplasm, causing further disease symptoms, sometimes of even higher intensity than during the actual activity of the Th1 disease itself. This can be likened to the Jarisch-Herxheimer Reaction which has been documented when killing bacterial pathogens, most notably when killing the *Treponema pallidum* which are believed to cause Syphilis.

This invention solves the problem of Herxheimer-induced anaphylaxis by targeting the bacterial genome—carefully controlling the pathogen's environment, as well as the antibiotic selection and dosing regimens.

Even if the patient is given a conventional dosage of the same antibiotics described in this invention, the antibiotics may fail to totally kill the pathogens, and if they do, there is the risk of a cytokine release sufficiently intense to cause life-threatening cardiac bradycardia or life-threatening pulmonary insufficiency, both of which were observed during experimentation with this invention.

This inventor has previously performed research on novel drug-dosing regimes in several diseases. In Diabetes I explored increased efficacy and reduced side-effects from a continuous infusion of Insulin, and in Cryptorchidism and Infertility I explored increased efficacy of pulsatile dosing of the hormones LH-RH and Gn-RH.

One of the best ways to administer a continuous concentration of any drug is by using an infusion pump, like the transcutaneous infusion pump for Insulin I invented in 1982: Marshall T G, Mekhiel N, Jackman W S, Perlman K, Albiser A M: New microprocessor-based insulin controller. IEEE Trans Biomed Eng. 1983 Nov.30(11):689-95.

During my Doctoral Research we also explored pulsatile administration of drugs, and my research group was able to cure Cryptorchidism and Infertility by using pulsatile injections of hormone, rather than using a continuous concentration: Keogh E J, MacKellar A, Mallal S A, Dunn A G, McColm S C, Somerville C P, Glatthaar C, Marshall T, Attikiouzel J: *Treatment of cryptorchidism with pulsatile luteinizing hormone-releasing hormone(LH-RH)*. J Pediatr Surg. 1983 Jun; 18(3):282-3.

It is typically believed that antibiotics administered at doses below the Minimum Inhibitory Concentration (MIC) are ineffective, and are likely to encourage the formation of antibiotic-resistant forms of the bacteria. However, when killing the antibiotic-resistant intra-cellular bacterial L-forms which cause AIDS and Cancer, I have discovered that antibiotics blocking bacterial protein synthesis by inhibiting the function of the 70S bacterial Ribosome are needed, and I have moreover discovered they are often optimally effective when delivered in a pulsatile fashion, wherein the peak concentration in the bloodstream may or may not be in excess of the MIC, but where the antibiotic concentration is allowed to decay away to a lower value before the next dose of antibiotic is given. It should be noted that the simplified pharmacokinetic model which is usually used to describe antibiotic absorption, anticipates an exponential rise of concentration to the peak value, and then a single exponential decay of that concentration (which is considered to be distributed within the plasma compartment). A pseudo-continuous concentration in the bloodstream can be achieved by dosing the drug at sufficient frequency that the next dose is absorbed before significant exponential decay from the previous dose.

The 70S Bacterial Ribosome

These L-form bacteria synthesize proteins (which they need for their survival) within a structure called a Ribosome. The bacterial ribosome is termed a '70S Ribosome' and it is conventionally divided into two subunits called the '30S' and the '50S' subunits.

The function of the 30S subunit is primarily determined by the 16S RNA of which it is primarily comprised, while the 50S subunit's function is primarily determined by the bacterial 23S RNA. Both subunit structures are completed by a variety of proteins and additional smaller RNA elements.

Antibiotics which inhibit the 30S subunit typically bind in the region near the helix which 'advances' during the transcription of bacterial mRNA to bacterial proteins. Antibiotics which inhibit the 50S subunit typically bind in the region where the tRNA docks, or in the region termed the Peptidyl Transferase Center (PTC), or in the region where the partially assembled protein travels through the body of the 50S subunit, prior to emerging as a completed protein from the ribosome.

Antibiotics which act by inhibiting actions of the 30S ribosomal subunit include Minocycline, Minocycline hydrochloride, Demeclocycline, Demeclocycline hydrochloride, Tigecycline, Tetracycline, Oxytetracycline, Doxycycline, Doxycycline hyclate, Spectinomycin, Hygromycin, Paromomycin, Streptomycin, Kanamycin, Gentamicin, Tobramycin, Amakacin, Netilmicin, Neomycin, Antibiotics which act by inhibiting actions of the 50S ribosomal subunit include Azithromycin, Clarithromycin, Clindamycin, Chloramphenicol, Linezolid, Erythromycin, Roxithromycin, Troleandomycin, Tylocin, Sparsomycin, Carbomycin A, Sparsomycin, Lincomycin, Cethromycin, Telithromycin, Tiamulin, Dalfopristin and Quinupristin.

The effectiveness of this invention is partially due to its control of the bacterial environment, and partially due to the use of antibiotics which act symbiotically on different areas of the ribosome, reducing the statistical likelihood that any bacteria species will have developed resistance mechanisms which simultaneously overcome all the methods being used by this invention to weaken protein synthesis by the ribosome.

The Vitamin D metabolites in Th1 Inflammation.

Th1 inflammation is customarily defined as inflammation which produces an inflammatory cytokine profile including significant 'Interferon-gamma.' Moreover, since this Th1 cytokine release also catalyzes the synthesis of the secosteroid hormone 1,25-dihydroxyvitamin-D (1,25-D) in the infected phagocytes, it is often possible to measure the proportion of 1,25-D which leaches into the bloodstream, together with plasma 25-hydroxyvitamin-D (25-D), and estimate the extent of Thi process in well-perfused, inflamed tissue.

One estimate of Th1 inflammation is performed by calculating the D-Ratio, the ratio of 1,25-D (in pg/mi) to the 25-D (in ng/ml). The value for a healthy population is 1.25, and this ratio is often elevated in Th1 immune disease because 25-D is down-regulated, and energetically converted to 1,25-D in the cytoplasm of the phagocytes and leukocytes. The conversion of 25-D to 1,25-D is catalyzed by the action of the cytokine Interferon-gamma. The measurement and prediction based on serum-based assays of the D-metabolites is only valid if the patient is not taking any supplements containing Vitamin D, and where the value of the presenting 25-D assay is between 14 ng/ml and 20 ng/ml.

This inventor has discovered that levels of 25-D higher than 25 ng/ml are associated with that metabolite exerting immunosuppression. It reduces innate immune activity by displacing 1,25-D from the ligand binding domain of the VDR and de-activating that receptor, preventing the transcription of genes essential to proper functioning of innate immunity.

Many investigators have noted that the level of 25-D falls below 20 ng/ml in patients with the Th1 inflammatory diseases, but that observation has not heretofore been recognized as a useful marker for the disease process itself. It has been mistakenly linked with an aberrant calcium metabolism. The calcium metabolism is, however, primarily regulated by the Para Thyroid Hormone (PTH) and the calcium-sensing receptor (CASR). See, for example: Thakker R V: *Disorders of the calcium-sensing receptor*. Biochim Biophys Acta. 1998 Dec. 10;1448(2):166-70.

Further data and information about the behavior of the D metabolites in Th1 inflammation can be found in this inventor's collaborative publication: Waterhouse J C, Marshall T G, Fenter B, Mangin M, Blaney G: *High levels of active 1,25-dihydroxyvitamin D despite low levels of the 25-hydroxyvitamin D precursor—Implications of dysregulated vitamin D for diagnosis and treatment of Chronic Disease. In Vitamin D: New Research. Volume* 1. Edited by: Stoltz V D. New York: Nova Science Publishers; 2006. ISBN: 1-60021-000-7

Optimally Effective Dosing Regimes for Ligands Acting as GPCR and NR Antagonists The subject compounds/ligands exhibit different affinities for different receptors. As the bloodstream concentration of each ligand is changed, they will have different effects on different receptors. An example chart showing such sensitivity variation for the ARBs is given in our paper "Marshall T G, Lee R E, Marshall F E: Common Angiotensin Receptor Blockers may directly modulate the immune system via VDR, PPAR and CCR2b. Theoretical Biology and Medical Modelling, not yet published" (draft attached).

Consequently the choice of ligands is important. One must employ ligands with good affinity for the receptors one wants to block, and with minimum affinity for those which are necessary for proper functioning of the body.

Additionally, the concentration of ligand in the bloodstream must be kept relatively constant, so as to help target those receptors which will enhance the health of the human body, and minimize the health of the pathogen(s).

This inventor has previously performed research on novel drug-dosing regimes in several diseases. In Diabetes, I explored increased efficacy and reduced side-effects from a continuous infusion of Insulin, and in Cryptorchidism and Infertility I explored increased efficacy of pulsatile dosing of the hormones LH-RH and Gn-RH.

During my Doctoral Research we also explored pulsatile administration of drugs, and my research group was able to cure Cryptorchidism and Infertility by using pulsatile injections of hormone, rather than using a continuous concentration: Keogh E J, MacKellar A, Mallal S A, Dunn A G, McColm S C, Somerville C P, Glatthaar C, Marshall T, Attikiouzel J: *Treatment of cryptorchidism with pulsatile luteinizing hormone-releasing hormone (LH-RH)*. J Pediatr Surg. 1983 Jun; 18(3):282-3.

One of the best ways to administer a continuous concentration of any drug is by using an infusion pump, for example the transcutaneous infusion pump for Insulin I invented in 1982: Marshall T G, Mekhiel N, Jackman W S, Perlman K, Albisser A M: *New microprocessor-based insulin controller*. IEEE Trans Biomed Eng. 1983 Nov.;30(11):689-95.

Other methods of administering semi-continuous concentrations of any drug are transcutaneous patches, sub-dermal implanted 'reservoirs', controlled-release drug compounding formulations, controlled-release binders (such as polymers) and implanted infusion pumps.

For example, the administration of Statins and ARBs at intervals beyond about 8 hours causes them to lose efficacy, because the concentration in the blood stream drops below the level at which a complete blockade of the undesirable receptors is effected. Thus, the conventional dosing of the ARBs that the FDA approved for hypertension, 24 hourly, with "the amount of return on twice daily dosing—already a poor investment," does not allow them to function effectively as pathogenic antagonists. They must be dosed much more frequently (preferably semi-continuously) so as to apply the maximum possible blockade to the Pathogenic Receptors in the inflamed tissue.

Special Considerations for Asserted Therapeutic or Pharmacological Utilities

With respect to MPEP 2107.03 "Special Considerations for Asserted Therapeutic or Pharmacological Utilities," the utility of this methods patent has been established by "statistically relevant data documenting the activity of a compound or composition, arguments or reasoning, documentary evidence (e.g., articles in scientific journals), or any combination thereof."

A sampling of peer-reviewed papers and conference presentations (from this inventor) sufficient to establish such utility, and which also document "actual evidence of success in treating humans" during the Phase 2 clinical studies conducted by this inventor, includes:

Marshall T G. What is the role of CWD bacteria during HIV infection? Invited Conference Presentation, 'Recovering from Chronic Disease', Jun. 17, 2006, Publisher: Autoimmunity Research Foundation (DVD transcript available)

Marshall T G: VDR Nuclear Receptor Competence is the Key to Recovery from Chronic Inflammatory and Autoimmune Disease. Abstract presentation, Days of molecular medicine, 2006. Copy available from URL http://autoimmunityresearch.org/karolinska-handout-.pdf Marshall T G, Lee R E, Marshall F E: Common Angiotensin Receptor Blockers may directly modulate the immune system via VDR, PPAR and CCR2b, Theoretical Biology and Medical Modelling,2006 Jan. 10;3(1):1. Available from URL http://www.tbiomed.com/content/3/1/1

Marshall T G: Molecular genomics offers new insight into the exact mechanism of action of common drugs—ARBs, Statins, and Corticosteroids. FDA CDER Visiting Professor presentation, FDA Biosciences Library, Accession QH447.M27 2006. Copy available from URL http://autoimmunityresearch.org/fda-visiting-professor-7mar06.ram Marshall T G, Marshall F E: Sarcoidosis succumbs to antibiotics—implications for autoimmune disease. Autoimmunity Reviews, 2004; 3(4):295-3001.

Waterhouse J C, Marshall T G, Fenter B, Mangin M, Blaney G: High levels of active 1,25-dihydroxyvitamin D despite low levels of the 25-hydroxyvitamin D precursor—Implications of dysregulated vitamin D for diagnosis and treatment of Chronic Disease. In Vitamin D: New Research. Volume 1. Edited by: Stoltz V D. New York: Nova Science Publishers; 2006. ISBN: 1-60021-000-7

Marshall T G, Fenter B J, Marshall F E: Antibacterial Therapy Induces Remission in Sarcoidosis (in English). JOIMR 2005;3(1):2 Available from URL http://www.joimr.org/phorum/read.php?f=2&i=107&t=107

Marshall T G, Fenter B, Marshall F E: Antibacterial Therapy Induces Remission in Sarcoidosis. Herald MKDTS 2004g; Volume III: Release 1. (The Journal of the Interregional Clinical-Diagnostic Center, Kazan, published in Russian translation). Invited Paper. Special issue on Sarcoidosis. ISSN: 1726-6149

Marshall T G, Fenter B, Marshall F E: Putative Antibacterial Mechanisms for Angiotensin Receptor Blockers. JOIMR 2004;2(2):1.

Marshall T G , Marshall F E : Sarcoidosis succumbs to antibiotics—implications for autoimmune disease. Autoimmunity Reviews,2004; Supplement 2:55 (Abstracts of 4th International Congress on Autoimmunity)

Marshall T G : Bacterial Th1 Processes Seem Key to Chronic Lyme Remission. ILADS conference, October 2004, Rye Town, N.Y.

Marshall T G : How *Borrelia* Evades the Immune System, and How we Help it Kill This Th1 Bacterium. '30 [th] Anniversary of Lyme Disease' conference, Farmington, Conn., May 7, 2005

Marshall T G , Mangin M, Marshall F E : Bacterial Th1 Processes Key to CFS/ME Remission. AACFS conference, Madison, Wis., October 2004

Marshall T G : Genomics, Molecular Medicine and Antibiotic Resistance. 'Recovery From Chronic Disease' conference, Chicago, Ill., Mar. 12, 2005.

DISCLOSURE OF "BEST METHOD" IMPLEMENTATION

The initial clinical study conducted by this inventor identified the following protocol as optimally efficient at killing the L-form bacterial pathogens. Patients were invariably unable to immediately commence at this dosing, and had to slowly increase to this antibiotic dose over a period of twelve, or more, months, due to severe and debilitating Jarisch Herxheimer Reaction as the intracellular pathogens were killed, and both white and red blood cells underwent apoptosis.

The best method is: Olmesartan Medoxomil administered 40 milligrams (mg) every 6 hours, together with the 30S ribosomal sub-unit inhibitor Minocycline Hydrochloride, 100 mg administered at a frequency of one dose every 48 hours; together with the 50S ribosoma sub-unit inhibitor Azithromycin, 125 mg administered at a frequency of one dose every 10 days; and the symbiotic 50S inhibitor Clindamycin, 150 mg administered at a frequency of one dose every 48 hours.

CONSIDERATION OF POTENTIAL 'PRIOR ART'

This invention is based on a thorough and complete knowledge of the pathogenesis of Chronic Disease which has been confirmed by Molecular Genomics, Molecular Biology, and a rapid-prototyping Phase 2 clinical trial.

This inventor recently delivered a presentation at the Karolinska Institute (home of Team Nobel) establishing this inventor's total scientific leadership in the understanding of the cause of, and the treatment of, chronic disease, including AIDS and Cancers: Marshall T G : *VDR Nuclear Receptor Competence is the Key to Recovery from Chronic Inflammatory and Autoimmune Disease. Abstract presentation, Days of Molecular Medicine,* 2006. Copy available from URL http://autoimmunityresearch.org/karolinska-handout.pdf This inventor recently featured in the plenary session of a scientific conference examining the bacterial pathogenesis for AIDS and Cancers: Marshall T G . *What is the role of CWD bacteria during HIV infection? Invited Conference Presentation, 'Recovering from Chronic Disease', Jun.* 17, 2006, Publisher: Autoimmunity Research Foundation (DVD transcript available)

This scientific leadership has resulted in an invention which stands on its own, where there really is no other previously filed patent application which covers the breadth of background, insight, the methods disclosed in, or the utility of, this patent application.

Nevertheless, the following US Patent Applications have been identified as those which should be examined as potentially containing material which, at first glance, might seem to portend "prior art."

U.S. Patent Application 200601 35422, "Use of Angiotensin receptor blockers (ARBs) to treat diseases associated with excess ACE," Inventor David W Moskowitz, describes a method of using Angiotensin Receptor Blocker Drugs (Sartans) in a number of chronic diseases. The Description includes AIDS and Cancers, although they do not seem to be specifically Claimed.

Firstly, this application does not contain prior art because it is deficient in its definition of the diseases for which the treatment is proposed. A number of diseases are named, and it is asserted that they are in some way "associated with excess ACE." Yet Angiotensin Converting Enzyme (ACE) excesses are primarily associated with the disease Sarcoidosis, which is not mentioned in this application (except in one of the citations). Even in that disease, lack of association, via both false positive and false negative, occurs in the majority of diagnoses (partly due to genotype variation), and it would be very difficult for an academic to sustain the argument that the disease process is "associated with excess ACE." The other diseases specified in the application are even less directly related to "excess Ace."

The inventor also fails to expound the impact of the various ACE genotypes on the disease process, instead focusing on D/D, and repeatedly citing his own hypothesis: Moskowitz D W. *Is angiotensin I-converting enzyme a "master" disease gene? Diabetes Technol Ther.* 2002;4(5):683-711. PMID: 12458570

Yet the theory advanced in that paper has subsequently been deprecated by a wealth of evidence. See, for example: "No relation was thus found between I/D polymorphism and susceptibility to sarcoidosis" (Alia P, etal: *Association between ACE gene I/D polymorphism and clinical presentation and prognosis of sarcoidosis. Scand J Clin Lab Invest.* 2005;65(8):691-7. PMID:16319043)

See also, for example, the review: Sayed-Tabatabaei F A, et al. *ACE polymorphisms. Circ Res.* 2006 May 12;98(9): 1123-3. PMID:16690893

The inventor has not contemplated that the ARB might be functioning as an antibacterial agent, or as an immunomodulatory agent. The patent does not disclose that L-form intraphagocytic bacteria are the root cause of the claimed diseases.

Further, the few clinical trails which that inventor conducted have failed to confirm the utility of the method proposed in his patent application. Application of this methodology, an ARB acting alone, in the majority of diseases mentioned in the application, has failed to confirm the inventor's disclosure of the functionality of his method, or even its utility, particularly in AIDS and Cancers. It cannot be considered to be "prior art."

U.S. Patent Application 200601 54975, "Modulators of the glucocorticoid receptor, AP-1, and/or NF-kB activity and use thereof" claims "A method of treating a disease or disorder which is associated with the expression product of a gene whose transcription is stimulated or repressed by glucocorticoid receptors, or a method of treating a disease or disorder associated with AP-1-and/or NF-.kappa.B-induced transcription" in Claim 11.

Paragraph 42 of that specification expounds that this definition is intended to include Cancers, and Paragraph 43 to include AIDS.

The problem with contemplating an omnibus patent such as this is to distinguish those attributes of the Claims which are not novel or useful, from those which possess both novelty and utility.

In this case, I would paraphrase this patent application to be similar in novelty and utility to one which claims "Prevention of death effected by ingestion of water." The most prolific GCR modulator was devised in 1954, a corticosteroid called Prednisone, and this drug has been used in all of the disease indications cited in the application. So there is no novelty there.

The novelty appears to come from the particular drug formula and configurations that are claimed as non-steroidal GCR modulators. Again, there is little novelty immediately evident because of the breadth of the claimed chemical description, which covers many drugs already patented and accepted to the pharmacopeia. A "best method" disclosure is not obviously present.

Significantly, that application does not disclose the effect of modulating the GCR. Indeed, since mice which are bred GCR-deleted do not survive gestation, there is very little knowledge available on the exact functions of the GCR.

I have disclosed in Table 1 that there are significant similarities between each of the Type 1 nuclear receptors, and their ligands. There is considerable functional overlap. It is difficult to imagine a GCR modulator which does not profoundly affect other Type 1 Nuclear Receptors. So I would even question the applicant's grasp of the field in which the invention is claimed.

In any case, that patent does not disclose which of the diseases cited in the application are caused by L-form bacteria, and does not disclose how the modulation of the GCR, as distinct from the other receptors, can be an effective treatment for the claimed diseases. It cannot be regarded as portending "prior art."

A search for Cell Wall Deficient Bacteria in Cancers and AIDS identified U.S. Patent Application 20050049207, "Method of treating and preventing cancer," inventor Doug A. Kaufmann.

Claim 1, upon which the other claims are based, is "A method of treating a mammal having cancer comprising administering to said mammal a formulation in an amount, at a frequency, and for a duration effective to reduce or eliminate said cancer, said formulation comprising an anti-fungal agent"

Even though that patent refers to Cell Wall Deficient organisms as the fundamental cause of Cancers, the anti-fungal agents canvassed in it do not have any relevance to the description or claims of my invention. It cannot be regarded as portending "prior art."

Indeed, an exhaustive search of the patent literature has confirmed the novelty of this invention, and confirmed that the scientific leadership contained in my peer-reviewed papers is matched by the utility of the disclosed method.

BRIEF DESCRIPTION OF THE DRAWINGS

Please note that the following figures show just a few examples of the implementation of this invention. For obvious reasons they do not show every ARB binding to every human and bacterial receptor, nor every statin (or other pharmaceutical drug with similar properties) binding to the subject genomes. They are necessary to demonstrate these preferred implementations, which would otherwise be difficult to communicate.

Color versions of these photographs have been forwarded by letter mail.

FIG. 10 shows the inter-atomic forces between the residues of the VDR and the atoms of 1,25-dihydroxyvitamin-D, the natural activator of the VDR (using 'Ligplot' standard software nomenclature). The view depicts inter-atomic forces when 1,25-D is docked into VDR.

FIG. 11 shows the inter-atomic forces between the residues of the VDR and the atoms of Olmesartan Medoxomil, a partial VDR Agonist. Note that there are strong interactions between Olmesartan and the residues Arg274, Tyrl 43, Ser275, SER278 and Ser237, which are essential for activation of the VDR. The view depicts Inter-atomic forces demonstrating Olmesartan as a partial agonist of VDR.

In Conclusion

Figure 1:
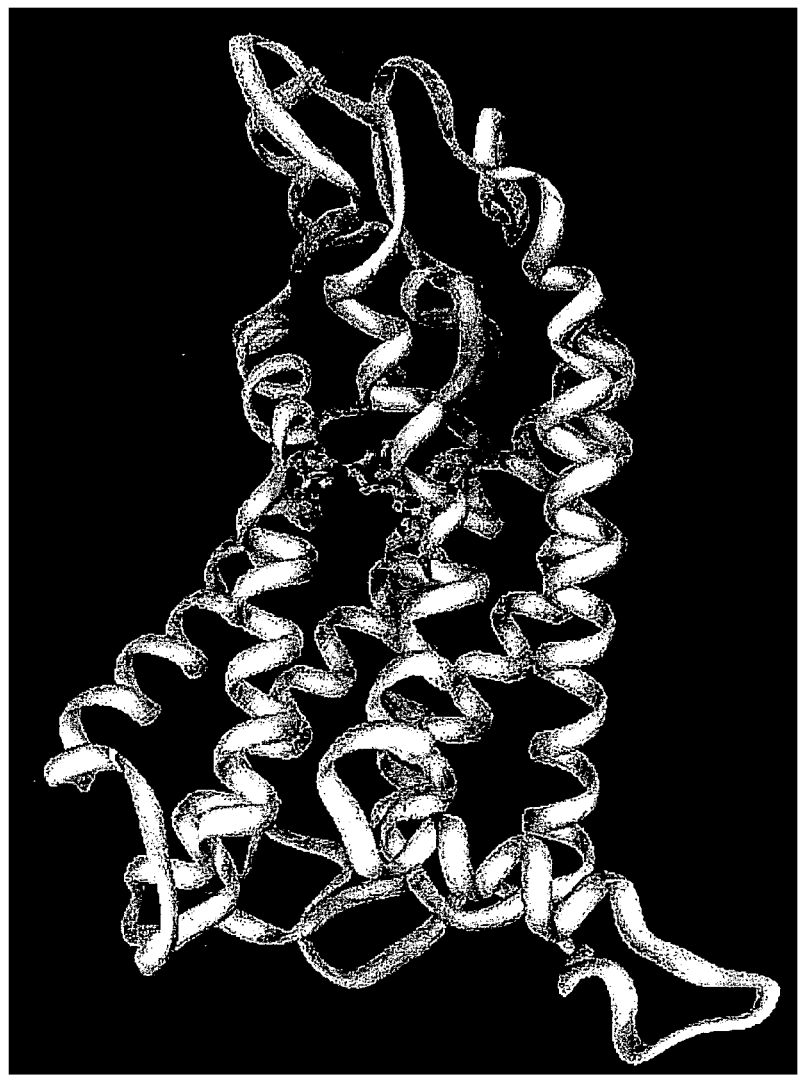
FIG. 1 is taken from the screen of a computer which is loaded with a model of the SAR0276 GPCR from the Methicillin-resistant *Staphylococcus aureus* (MRSA) 'superbug' MRSA252, the GPCR called Swiss-Prot:Q6GK32$_{13}$ STAAR, obtained with the procedures described in my paper "*Common Angiotensin Receptor Blockers may directly modulate the immune system via VDR, PPAR and CCR2b*" (attached). The GPCR is shown as a customary helix-sheet diagram rather than by showing the thousands of tiny atoms which comprise its detail. An example Angiotensin Receptor Blocker, 'Olmesartan,' is tightly bound (Ki=0.9 nmol) in a de-activating location of this GPCR (olmesartan is the dark grey structure). The MRSA bacterium containing this GPCR would not be able to function as effectively once the Olmesartan had attacked this GPCR. The view depicts Olmesartan docked into MRSA species GPCR SAR0276 with Ki=0.9 nmol.
Figure 2:
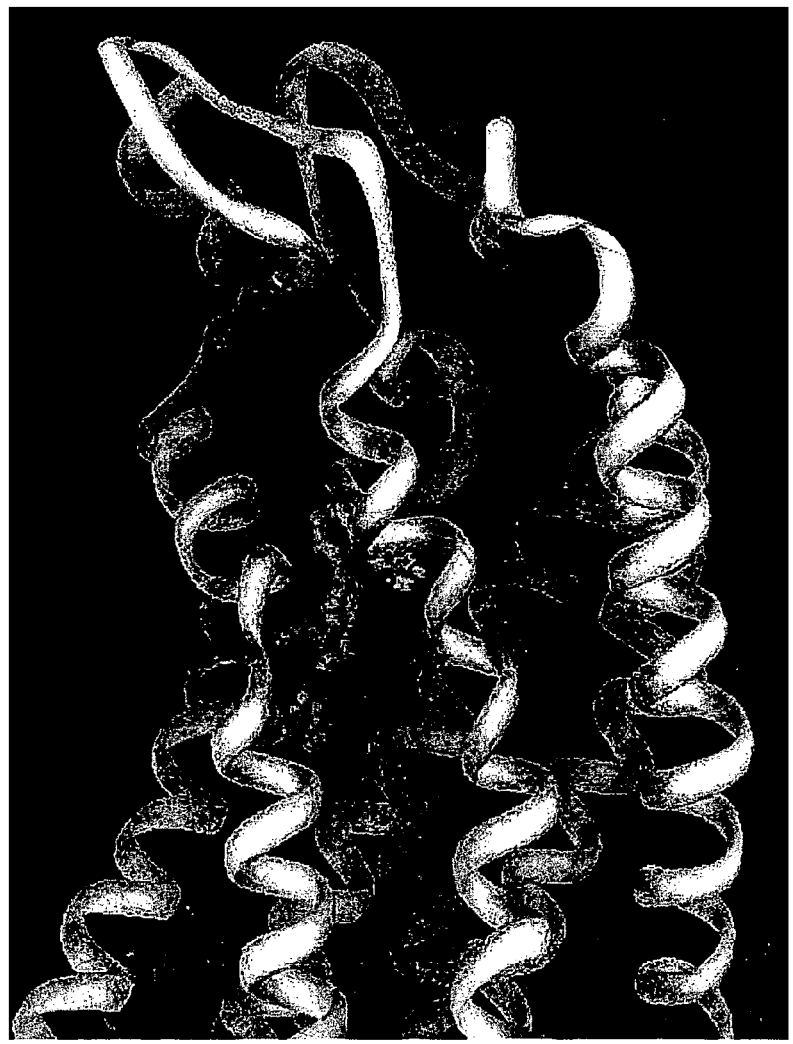
FIG. 2 shows Olmesartan attacking a GPCR (Swiss-Prot: BB0006) from the Genome of '*Borrelia burgdorferi*', the species which causes, inter alia, Lyme Disease. The Olmesartan is binding with high efficiency, Ki=0.7 nanomolar. The view depicts Olmesartan docked into *Borrelia Burgdorferi* GPCR bb0006, Ki=0.7 nmol.
Figure 3:
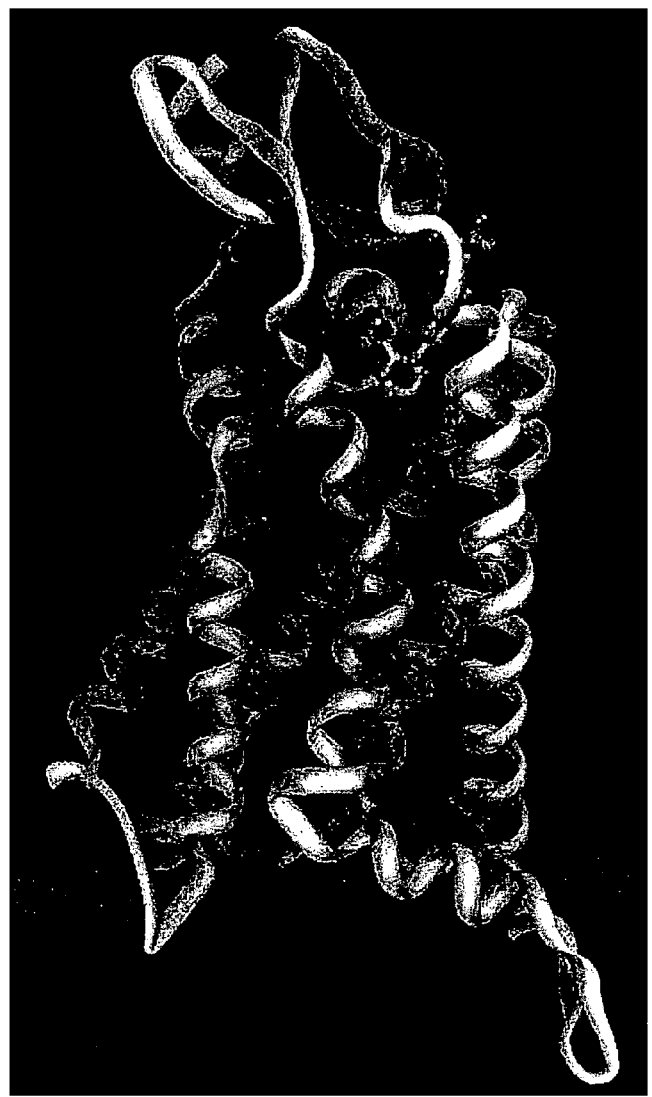
FIG. 3 shows Olmesartan inhibiting a GPCR (Swiss-Prot: RP630) from the species '*Rickettsia prowazekii*,' another ubiquitous human pathogen. Here the ligand is bound even more tightly, with Ki=0.2 nmol. The view depicts Olmesartan docked into *Rickettsia* GPCR rp630, Ki=0.2 nmol.
Figure 4:
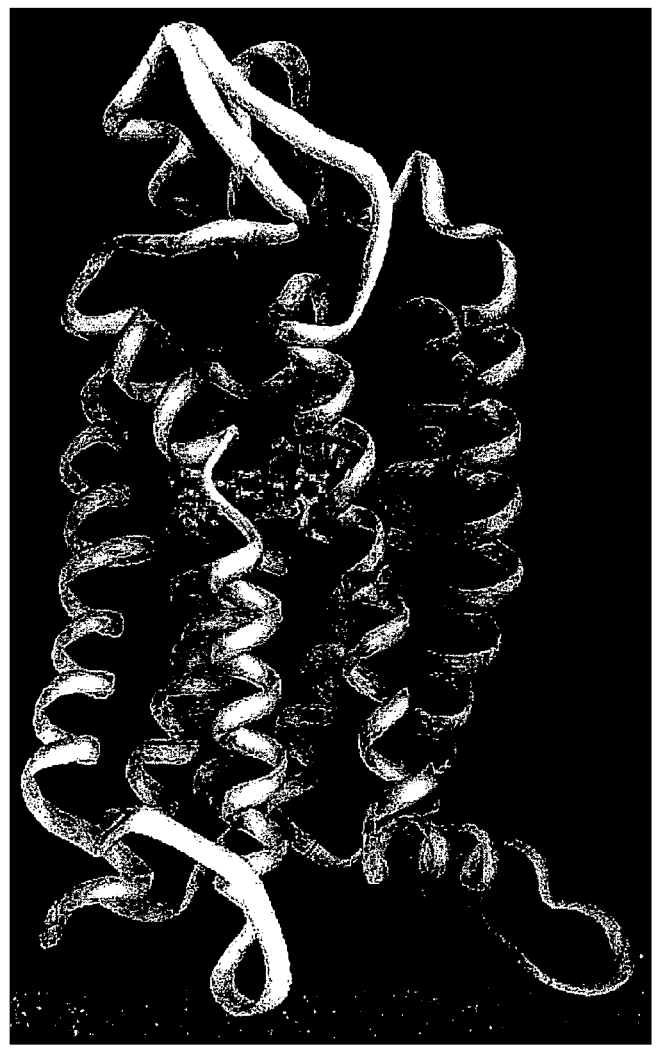
FIG. 4 shows Olmesartan bound to a GPCR (ydgG) from the species '*E-coli*' with Ki=0.3 nmol, clearly stopping it from functioning as the bacterium would wish. The view depicts Olmesartan docked into *E-coli* GPCR ydgG, Ki=0.3 nmol.
Figure 5:
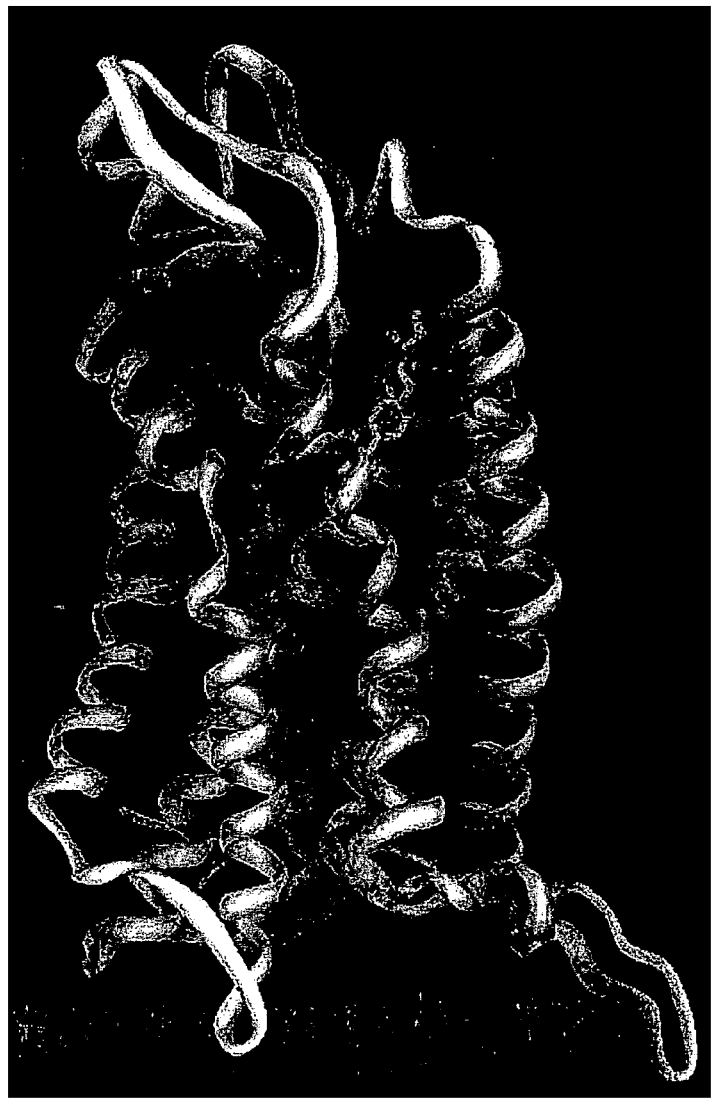
FIG. 5 shows Olmesartan bound to the GPCR protein from *Mycobacterium Tuberculosis* (Swiss-Prot:MT1133) with Ki=1.7 nmol. Again, the full functioning of this terrible bacterium is being inhibited by the ligand. The view depicts Olmesartan docked in *Mycobacterium Tuberculosis* GPCR mt1133, Ki=1.7 nmol.
Figure 6:
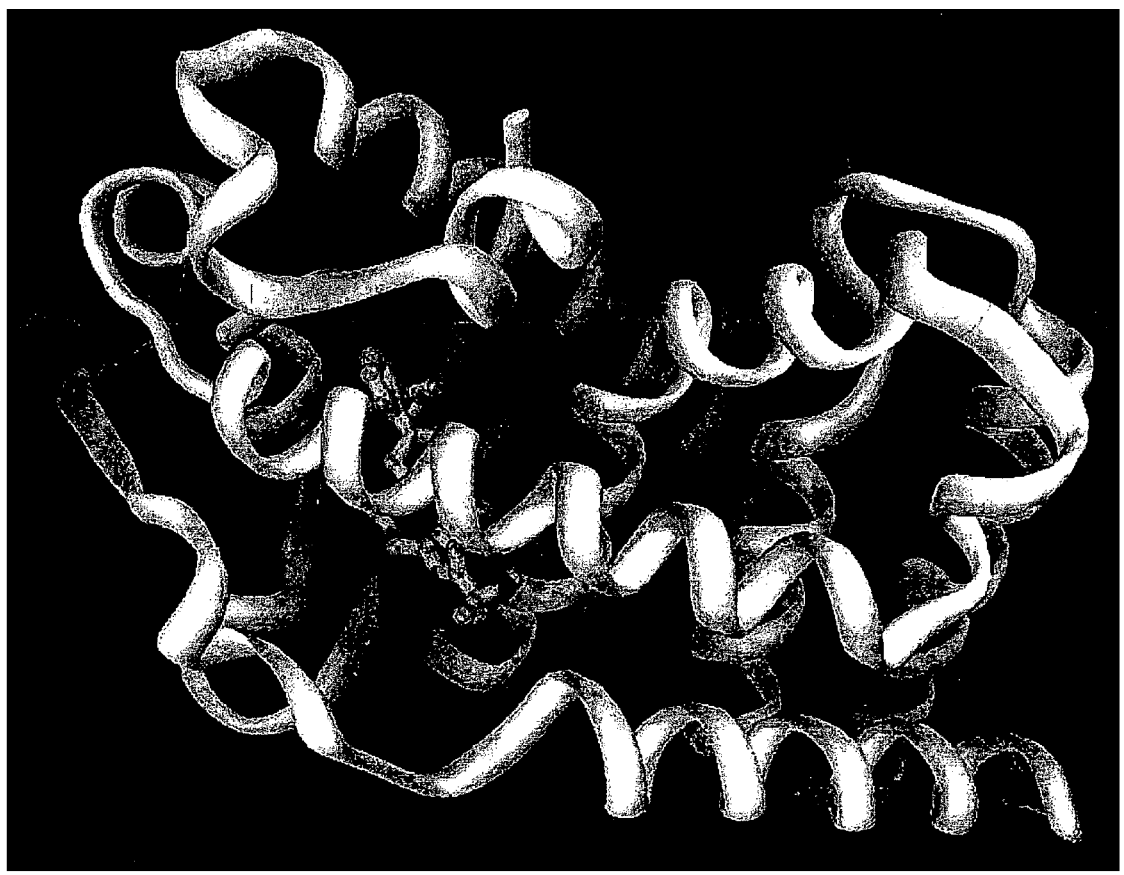
FIG. 6 shows Olmesartan bound into the *Homo sapiens* VDR NR, with an affinity Ki=10 nmol. Geometric analysis shows high affinity for the helix containing residues Ser278, Arg 274 and Ser 275, and also for the helices containing Ser237 and Tyr143. It is to be expected that anchoring these helices geometrically in space will activate the VDR, and Olmesartan is therefore a partial VDR Agonist (see FIGS. 10, 11 for detailed atomic interaction graphs showing the forces exerted between the VDR residues and Olmesartan Medoxomil, and 1,25-D.
Figure 7:
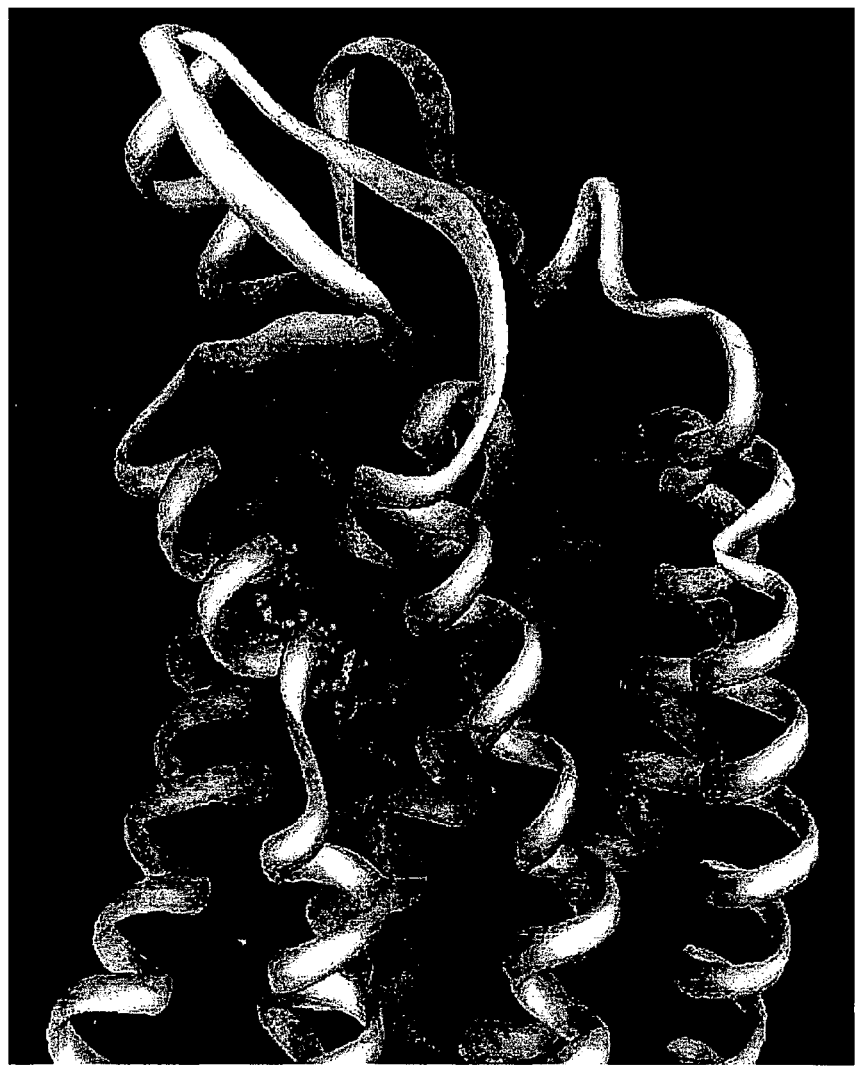
FIG. 7 shows the Statin 'Simvastatin' bound into the GPCR protein SAR0276 from MRSA252 with Ki=4.4 nmol. The view depicts Simvastatin docked into MRSA252 GPCR SAR0276 with Ki=4.4 nmol.
Figure 8:
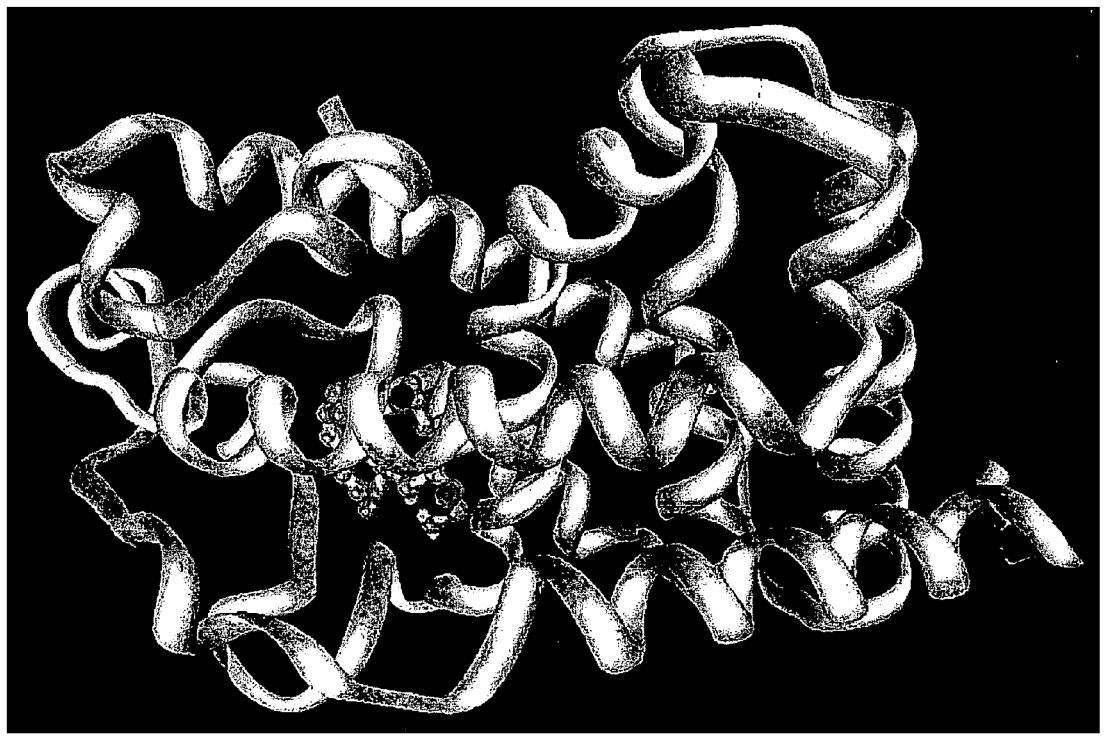
FIG. 8 shows the Statin Lovastatin bound into the *Homo sapiens* VDR with Ki=9.6 nmol. The view depicts Lovastatin docked into *Homo sapiens* VDR, Ki=10 nmol.
Figure 9:
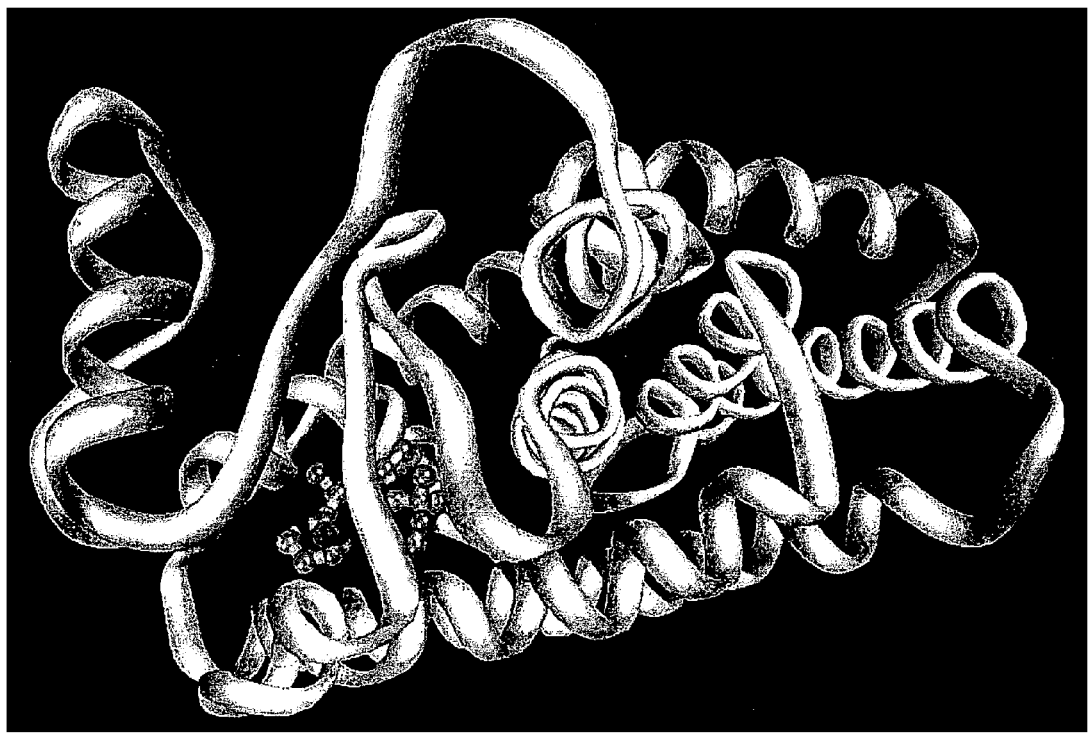
FIG. 9 shows Simvastatin bound into the *Homo Sapiens* PPAR with Ki=0.3 nmol. The view depicts Simvastatin docked into *Homo sapiens* PPAR, Ki=0.3 nmol.
Figure 10:
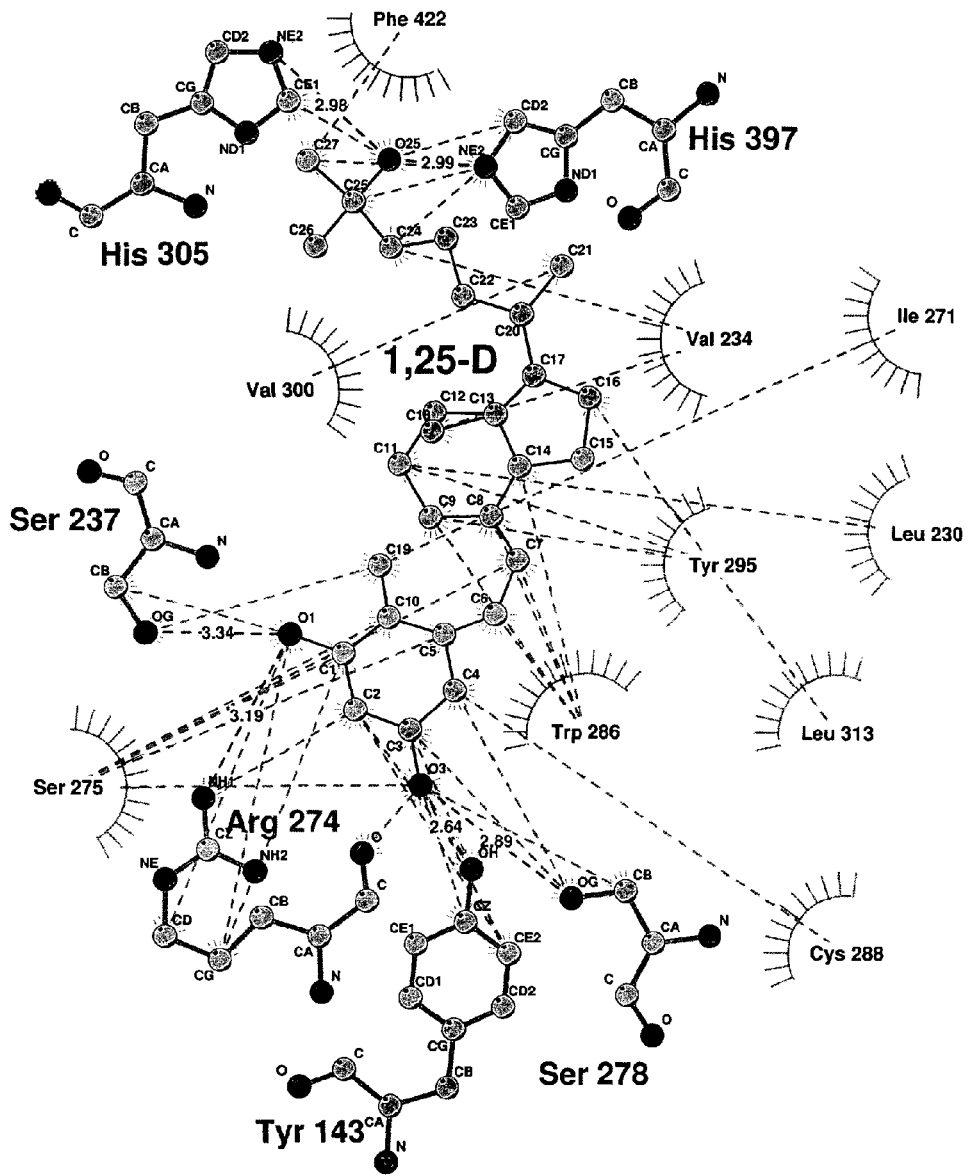
FIGS. 10 and 11 allow more detailed analysis of the Agonistic action of Olmesartan Medoxomil and the VDR). The view depicts Olmesartan docked into *Homo sapiens* VDR, Ki=10 nmol.
Figure 11:
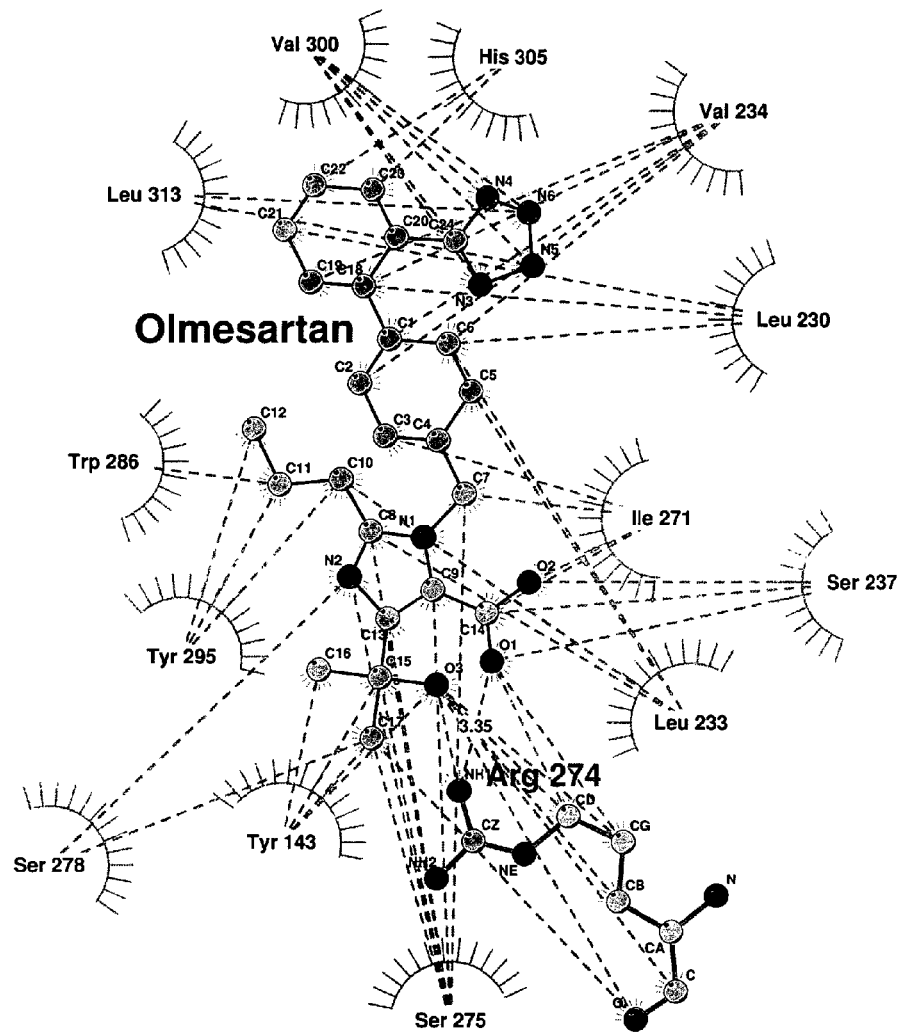
Figure 11:
Figure 11:
Figure 12:
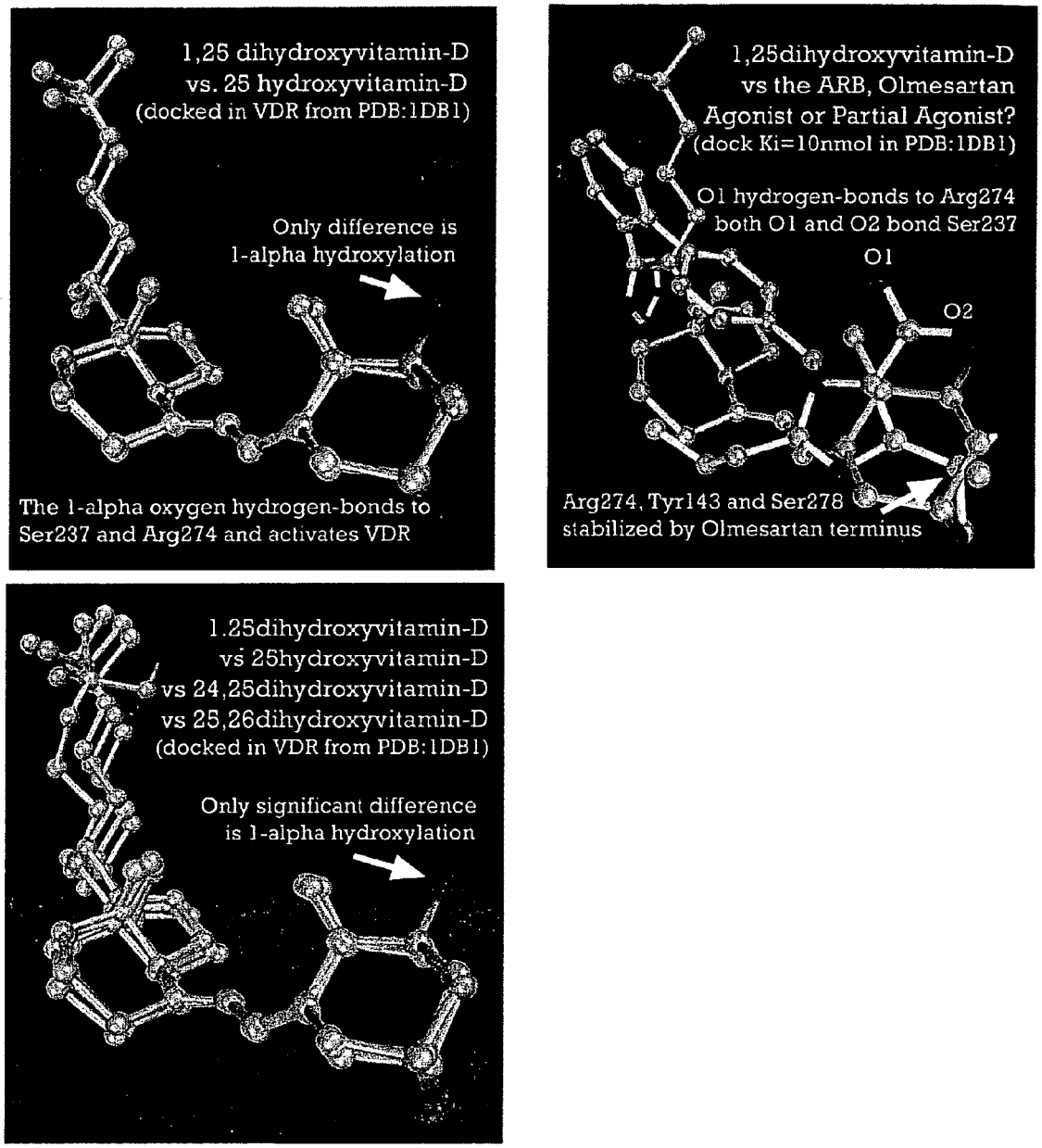
FIG. 12 shows the position of the Vitamin D metabolites when docked into the VDR at the point of lowest energy. Note that, of all the D metabolites, only 1,25-D has the 1-alpha hydroxylation necessary to activate the receptor (note that Olmesartan Medoxomil has an oxygen in a symbiotic position, which is why it can act as an agonist). The view depicts overlayed docked atomic positions showing the only D metabolite capable of binding residues Arg274 and Ser237, activating VDR, is 1,25-D, while O1 and O2 of Olmesartan perform that function, and make Olmesartan a partial VDR agonist.
Figure 13:
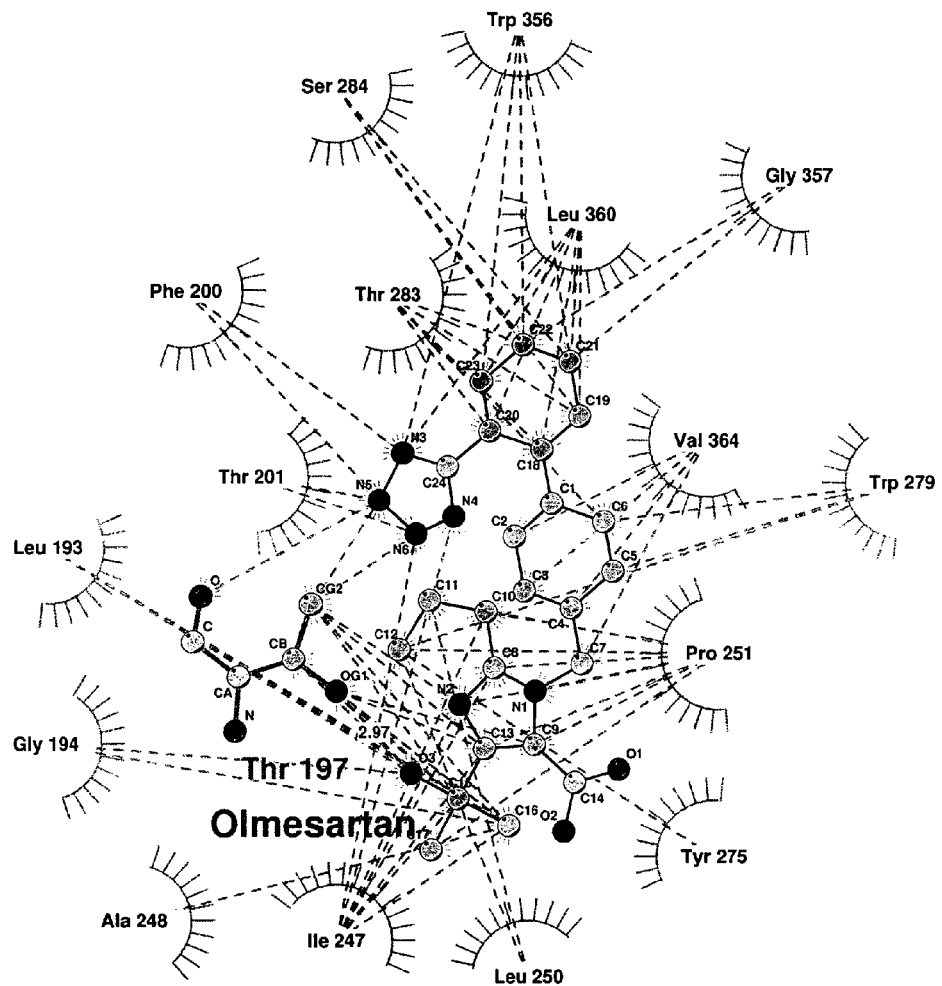
FIG. 13 shows shows the inter-atomic forces between Olmesartan Medoxomil and the residues of a putative CB1 receptor, docked as a partial agonist, with affinity Ki=3 nanomolar. The view depicts Olmesartan Medoxomil docked in CB1 receptor (Ki=3nmol).

It will be clear that the invention may be practiced otherwise than as particularly described in the foregoing description and examples. Numerous modifications and variations of the present invention are possible in light of the above teachings and, therefore, are within the scope of the appended Claims.

What is claimed is:

1. A method for reducing risk of an inflammatory-induced disease caused by intra-phagocytic prokaryotic pathogens, wherein the inflammatory-induced disease is selected from the group consisting of Bladder Cancer, Breast Cancer, Colorectal Cancer, Gastric Cancer, Liver Cancer, Lung Cancer, Pancreatic Cancer, Prostate Cancer, and Thyroid Cancer; comprising administering to a subject in need thereof a therapeutically effective amount of Olmesartan or Olmesartan medoxomil, together with one or more antibiotics capable of inhibiting bacterial protein synthesis by inhibiting the intra-phagocytic prokaryotic 70S-bacterial-ribosome to treat intra-phagocytic prokaryotic pathogens and reduce the risk of an inflammatory-induced disease, wherein the Olmesartan or Olmesartan medoxomil is administered by semi-continuous or intermittent administration in such a way that the Olmesartan or Olmesartan medoxomil has a concentration in the subject's bloodstream that is constrained from falling below 30% of its peak value.

2. The method defined in claim 1 wherein the Olmesartan or Olmesartan medoxomil is administered by using a method of semi-continuous administration selected from the group consisting of trans-cutaneous-patch, implanted infusion device, implanted drug delivery system, external infusion device, trans-cutaneous delivery system, and continuous IntraVenous infusion.

3. The method defined in claim 1 wherein the Olmesartan or Olmesartan medoxomil is administered by using a method of intermittent administration selected from the group consisting of oral dosing at intervals sufficiently small to stabilize the ARB level in the subject's bloodstream between 30% and 100% of its peak value, injections at intervals sufficiently small to stabilize the ARB in the subject's bloodstream level between 30% and 100% of its peak value, intermittent IntraVenous (IV) at intervals sufficiently small to stabilize the ARB level in the subject's bloodstream between 30% and 100% of its peak value, and trans-cutaneous infusion at intervals sufficiently small to stabilize the ARB level in the subject's bloodstream between 30% and 100% of its peak value.

4. The method defined in claim 1 wherein the Olmesartan or Olmesartan medoxomil is administered using a technique designed to slow the release, or to slow the absorption, of the Olmesartan or Olmesartan medoxomil and thus stabilize its level in the subject's bloodstream at between 40% and 100%, where such technique is selected from the group consisting of formulation with polymers, substances known as sustained-release binders, and other semi-soluble compounds.

5. The method defined in claim 1 wherein the antibiotic is a 30S Bacterial Ribosomal subunit inhibitor selected from the group consisting of Minocycline, Minocycline hydrochloride, Demeclocycline, Demeclocycline hydrochloride, Tigecycline, Tetracycline, Oxytetracycline, Doxycycline, Doxycycline hyclate, Spectinomycin, Hygromycin, Paromomycin, Streptomycin, Kanamycin, Gentamicin, Tobramycin, Amikacin, Netilmicin, and Neomycin.

6. The method defined in claim 1 wherein the antibiotic is a 30S Bacterial Ribosomal subunit inhibitor selected from the group consisting of The Tetracycline family of antibiotics.

7. The method defined in claim 6 wherein the 30S Bacterial Ribosomal subunit inhibitor antibiotic is administered with a pulsatile dosing frequency between once every 36 hours and once every 8 days, such that the concentration of the antibiotic in plasma is allowed to drop below the minimum inhibitory concentration before the next dose of antibiotic is administered.

8. The method defined in claim 1 wherein the antibiotic is a 50S Bacterial Ribosomal subunit inhibitor selected from the group consisting of Azithromycin, Clarithromycin, Chloramphenicol, Linezolid, Erythromycin, Roxithromycin, Troleandomycin, Tylocin, Carbomycin A, Clindamycin, Lincomycin, Cethromycin, Telithromycin, Sparsomycin, Tiamulin, Dalfopristin, and Quinupristin.

9. The method defined in claim 8 wherein the 50S Bacterial Ribosomal subunit inhibitor antibiotic is administered with a pulsatile dosing frequency between once every 36 hours and once every 21 days, such that the concentration of the antibiotic in plasma is allowed to drop below the minimum inhibitory concentration before the next dose of antibiotic is administered.

10. The method defined in claim 1 wherein the 70S bacterial-ribosome is inhibited by two or more antibiotics selected so that both the 30S and 50S subunits are symbiotically inhibited from full bacterial protein synthesis.

11. The method defined in claim 10 wherein the 70S ribosome is inhibited by one 30S subunit inhibiting antibiotic selected from the group consisting of Minocycline, Minocycline hydrochloride, Demeclocycline, Demeclocycline hydrochloride, Tigecycline, Tetracycline, Oxytetracycline, Doxycycline, Doxycycline hyclate, Spectinomycin, Hygromycin, Paromomycin, Streptomycin, Kanamycin, Gentamicin, Tobramycin, Amikacin, Netilmicin, and Neomycin; together with one or more 50S subunit inhibiting antibiotics selected from the group consisting of Azithromycin, Clarithromycin, Clindamycin, Chloramphenicol, Linezolid, Erythromycin, Roxithromycin, Troleandomycin, Tylocin, Carbomycin A, Sparsomycin, Lincomycin, Cethromycin, Telithromycin, Tiamulin, Dalfopristin, and Quinupristin.

12. The method defined in claim 11 wherein some, or all, of the antibiotics are administered with a pulsatile dosing frequency between once every 36 hours and once every 21 days, so that the concentration of the antibiotic in plasma is allowed to drop below the minimum inhibitory concentration before the next dose of antibiotic is administered.

13. The method defined in claim 1 wherein the one or more 70S bacterial-ribosome-inhibiting antibiotics comprise one 30S ribosomal sub-unit inhibiting antibiotic selected from the group consisting of Minocycline, Minocycline hydrochloride, Demeclocycline, and Demeclocycline hydrochloride; together with Azithromycin 50S subunit inhibiting antibiotic; wherein the 30S ribosomal sub-unit inhibitor is administered at a frequency between 36 hours and 8 days; and wherein the Azithromycin is administered at a frequency between 6 days and 21 days.

14. The method defined in claim 1 wherein the one or more 70S bacterial-ribosome-inhibiting antibiotics comprise one selected from the group consisting of inhibitors of the 30S ribosomal sub-unit Minocycline, Minocycline hydrochloride, Demeclocycline, Demeclocycline hydrochloride, Tigecycline, Tetracycline, Oxytetracycline, Doxycycline, Doxycycline hyclate, Spectinomycin, Hygromycin, Paromomycin, Streptomycin, Kanamycin, Gentamicin, Tobramycin, Amikacin, Netilmicin and Neomycin; together with one selected from the group consisting of the 50S subunit inhibiting antibiotics which bind near the PTC Clindamycin, Dalfopristin, Chloramphenicol, Linezolid, Tiamulin, and Lincomycin.

15. The method defined in claim 1 wherein the one or more 70S bacterial-ribosome-inhibiting antibiotics comprise one antibiotic from the group consisting of the 30S subunit inhibitors Minocycline, Minocycline hydrochloride, Demeclocycline, Demeclocycline hydrochloride, Tigecycline, Tetracycline, Oxytetracycline, Doxycycline, Doxycycline hyclate, Spectinomycin, Hygromycin, Paromomycin, Streptomycin, Kanamycin, Gentamicin, Tobramycin, Amikacin, Netilmicin and Neomycin; together with an antibiotic from the group consisting of the 50S subunit inhibitors Azithromycin, Clarithromycin, Erythromycin, Roxithromycin, Troleandomycin, Tylocin, Carbomycin A, Sparsomycin, Lincomycin, Cethromycin, Telithromycin, and Quinupristin; together with one selected from the group consisting of the 50S subunit inhibiting antibiotics which bind near the PTC Clindamycin, Dalfopristin, Chloramphenicol, Linezolid, Tiamulin, and Lincomycin.

16. The method defined in claim 1 wherein the one or more 70S bacterial-ribosome-inhibiting antibiotics comprise one antibiotic from the group consisting of the 30S subunit inhibitors Minocycline, Minocycline hydrochloride, Demeclocycline, Demeclocycline hydrochloride, Tigecycline, Tetracycline, Oxytetracycline, Doxycycline, Doxycycline hyclate, Spectinomycin, Hygromycin, Paromomycin, Streptomycin, Kanamycin, Gentamicin, Tobramycin, Amikacin, Netilmicin and Neomycin; together with two symbiotic 50S subunit inhibiting antibiotics Azithromycin and Clindamycin; wherein the 30S subunit inhibitor is administered at a frequency between 36 and 8 days; wherein the Azithromycin is administered at a frequency between 6 and 21 days; and wherein the Clindamycin is administered at a frequency between 36 hours and 21 days.

17. The method defined in claim 1 wherein two 70S bacterial-ribosome-inhibiting antibiotics are selected, one from the group consisting of the 50S subunit inhibitors Azithromycin, Clarithromycin, Erythromycin, Roxithromycin, Troleandomycin, Tylocin, Carbomycin A, Sparsomycin, Lincomycin, Cethromycin, Telithromycin, and Quinupristin; together with one selected from the group consisting of the 50S subunit inhibiting antibiotics which bind near the PTC Clindamycin, Dalfopristin, Chloramphenicol, Linezolid, Tiamulin, and Lincomycin.

18. The method defined in claim 1 wherein 40 mg of Olmesartan Medoxomil is administered every 6 hours, 100 mg of Minocycline hydrochloride is administered every 48 hours, and 125 mg of Azithromycin is administered every 10 days.

19. The method defined in claim 18, further wherein 150 mg of Clindamycin is administered every 48 hours.

* * * * *